United States Patent [19]
Hsia

[11] 3,954,409
[45] May 4, 1976

[54] METHOD FOR DETERMINING SERUM CHOLESTEROL BINDING RESERVE AND USE IN DIAGNOSIS

[76] Inventor: Sung Lan Hsia, c/o Department of Dermatology, University of Miami School of Medicine, P.O. Box 520875 Biscayne Annex, Miami, Fla. 33152

[22] Filed: Apr. 22, 1974

[21] Appl. No.: 462,818

[52] U.S. Cl............................................. 23/230 B
[51] Int. Cl.$^2$......................................... G01N 33/00
[58] Field of Search.................. 23/230 B; 252/408

[56] References Cited
UNITED STATES PATENTS

| | | | |
|---|---|---|---|
| 3,001,950 | 9/1961 | Hopper......................... | 23/230 B X |
| 3,479,154 | 11/1969 | Cardinal........................... | 23/230 B |
| 3,736,263 | 5/1973 | Parekh et al.................. | 23/230 B X |
| 3,799,739 | 3/1974 | Warburton...................... | 23/230 B |

OTHER PUBLICATIONS
J. Clin. Invest., Vol. 52, pp. 1467–1469 (1973).

Primary Examiner—Morris O. Wolk
Assistant Examiner—Timothy W. Hagan

[57] ABSTRACT

The ability of serum to bind cholesterol in soluble lipoprotein complexes is believed to retard the deposition of cholesterol in atherosclerotic plaques. This ability is measured by "serum cholesterol binding reserve" (SCBR), defined as the amount of exogenous cholesterol which a serum specimen is capable of solubilizing in addition to its cholesterol content. A method for determining SCBR has been developed. An excess amount of cholesterol is added to a sample of blood serum and incubated. The amount of cholesterol solubilized by the serum is then measured. Test results in case-control studies of premature myocardial infarction have demonstrated the usefulness of SCBR in assessing the risk of coronary heart disease.

8 Claims, 2 Drawing Figures

METHOD FOR DETERMINING SERUM CHOLESTEROL BINDING RESERVE AND USE IN DIAGNOSIS

The invention described herein was made in the course of work under a grant or award from the Department of Health, Education, and Welfare.

This invention relates to a process for determining the serum cholesterol binding reserve of a person's blood, and to the use of such data as a diagnostic tool for early warning of atherosclerosis and the risk of coronary heart disease. More particularly, this invention relates to a practical and reproducible method for determining the serum cholesterol binding reserve of human blood, and the use of the determined value in diagnosis.

Clinical or laboratory means for estimating accurately the degree and extent of atherosclerosis are still lacking. Definitive diagnosis usually is made after the appearance of an overt complication due to thrombosis of an artery or infarction of an organ. A presumptive diagnosis can be made on the basis of the symptoms and signs of ischemia, especially as regards the arteries to the brain, heart and lower extremities.

Diagnostic tools for early warning are limited. The laboratory finding of hypercholesteremia (total blood cholesterol greater than 250 mg/100 ml) is suggestive. Angiocardiography may be helpful in demonstrating vessel calcification with or without obstruction. Abnormalities in the resting electrocardiogram (ECG) or changes in the post-exercise tracing, frequently are of diagnostic value. Oscillometric studies may be useful in lesions involving the lower extremities.

In the United States over half of the deaths are caused by cardiovascular diseases. Heart attack usually strikes suddenly, without warning, and often at the prime of the victim's life; yet the underlying cause, atherosclerosis, may have been in progress for many years leading to the sudden cardiac arrest. Statistical data compiled by epidemiologic studies have given strong evidence for an association between high levels of serum lipids, especially of cholesterol, to the incidence of coronary heart disease. Yet many people are known to have relatively high serum cholesterol levels and go on for many years without overt cardiac troubles, while others having lower levels succumb to heart attacks. Although the association between the level of serum cholesterol and coronary heart disease has been well documented, diagnostic tests with greater predictive value are manifestly needed.

There is evidence that the cholesterol deposited in atheroma of the arterial wall originates from the blood serum. It is believed that higher concentrations of cholesterol in blood serum enhance plaque formation, while on the other hand the ability of the serum to keep cholesterol in the form of soluble lipoprotein complexes is an opposing factor which retards the process. Without being limited by any theory of action, it is now proposed that the ability of the serum to bind cholesterol in the form of soluble lipoprotein complexes has a protective function in retarding the deposition of cholesterol in atheroma. Accordingly, the serum cholesterol binding reserve, (herein designated SCBR) which is a measure of this ability should be a useful factor for predicting the risk of coronary events, i.e. the lower the SCBR the higher the tendency to develop atherosclerosis and hence the higher the risk of coronary heart disease. By definition, serum cholesterol binding reserve (SCBR) is the amount of cholesterol which the serum can dissolve in addition to the cholesterol already present in the serum (herein designated as serum cholesterol, SC). Both SCBR and SC are expressed in milligrams of cholesterol per 100 ml of serum. As elevated levels of serum cholesterol (SC) are associated with a high risk of coronary heart disease, the ratio SCBR/SC, and the degree of saturation of the serum lipoproteins with cholesterol, as determined by SC/(SC+ SCBR), should be more significant than SC alone in predicting coronary heart disease and atherosclerosis.

A method has now been developed for determining SCBR; and the values of SCBR, SC, the ratio SCBR/SC, and the degree of saturation of serum with cholesterol, which is SC/(SC + SCBR), have been compared in cases of known myocardial infarction and matched controls. The results indicated that SCBR is a better discriminant between the cases and controls than SC. The values of SCBR, SCBR/SC and SC/(SC + SCBR) are therefore useful in predicting the risk of coronary heart disease, as discussed more fully below.

A method suitable for the determination of the serum cholesterol binding reserve comprises the steps of:

a. admixing in predetermined amounts an excess amount of finely divided cholesterol with a specimen of blood serum;

b. incubating the mixture for a period of time and at temperatures sufficient to maximize the solubilization of cholesterol in the serum while obtaining continuous contact of said serum with said cholesterol by suitable means;

c. separating the incubated serum of step (b) from the excess of cholesterol; and thereafter d. measuring the amount of cholesterol in said incubated serum, and subtracting from this amount the measured cholesterol content of a reference specimen of the same serum prior to incubation with cholesterol.

Known methods for incorporation of cholesterol into serum lipoproteins require prolonged incubation and give large variations in the quantity of cholesterol taken up by a given serum with the result that such procedures are not suitable for obtaining comparable and reproducible results for determination of SCBR. These difficulties are overcome in step (a) of this invention by pulverizing the cholesterol into very small particles.

Pulverization of Cholesterol

To enhance the rate of uptake of cholesterol by the serum, crystalline cholesterol is pulverized, and the amount of pulverized cholesterol used in each incubation is in sufficiently large excess to assure maximum uptake. For example, commercial grade cholesterol is suspended in water and the suspension subjected to sonication while cooling in an ice bath. The temperature is maintained within the range of about 0° to 10°C by alternating sonication periods of a few minutes with cooling periods of a few minutes. In practice, good results are obtained by sonication for about seven 2 minute intervals with about 2 minute interruptions. More extended times for sonication has been found unnecessary, but doubling the time of sonication will not affect the results adversely.

Instead of sonication, various preparations of cholesterol dispersed on supporting powderous materials such as Celite, Gas-chrom S, or other inert solid material have been tested. The solid supporting material also includes water soluble substances, such as solid sodium chloride crystals, from which a finely divided cholesterol is separated readily by dissolving out the water soluble sodium chloride after mixing with serum. This method reduces the time required for sedimentation prior to filtering in the next step. These materials, however, have shown larger variations in the quantity of cholesterol taken up by a given serum and consequently give less precise results. It is also necessary to take into consideration the shelf-life of the particular product, with or without an additive to avoid aggregation or formation or large cholesterol crystals on the solid material. The shelf-life of preparations of Celite coated with cholesterol, for example, are stabilized by additives such as mineral oils, diethylene glycol succinate, castor oil, sesame oil, pump oil, and oleic acid. But these additives can alter the results of the determination. Since the next step in the procedure requires incubation of the serum with dispersed cholesterol for long hours, antibiotics are added, if needed, to inhibit bacterial growth. Gentamicin sulfate is satisfactory for this purpose because it is active against a wide spectrum of bacteria and is relatively stable. Other bacteriocides can be used, as is known in the art.

Serum Storage

Storage of the serum at room temperature or at 6°C for more than 2 days causes changes in SCBR. It is therefore important that the determination of SCBR be performed within 48 hours after the blood has been drawn or that the serum be stored immediately at −20°C or below.

TABLE 1

Stability of SCBR of a serum during storage

| Temperature of Storage | Duration | SCBR |
|---|---|---|
| | days | mg/100 ml |
| 22°C | 0 | 92 |
| | 1 | 89 |
| | 2 | 93 |
| | 5 | 127 |
| | 7 | 140 |
| 6°C | 2 | 104 |
| | 10 | 112 |
| | 14 | 110 |
| −20°C | 25 | 98 |

The above shows the values of SCBR of a serum specimen after storage at room temperature (22°C), in the refrigerator (6°C) and in the freezer (−20°C). The value of SCBR tended to increase slightly in 2 to 3 days when the serum was stored at room temperature or at 6°C, but remained unchanged after 25 days when it was kept frozen at −20°C. SCBR of 7 serum specimens was determined before and after storage of the sera at −20°C for 7 months. The variation in values was within the error of the method of determination. A serum specimen having SCBR of 66 mg/100 ml was heated at 58°C, and SCBR increased to 87 mg/100 ml after 10 minutes, and to 99 mg/100 ml after 2 hours.

In step (b) pulverization of cholesterol by sonication greatly accelerates its rate of solubilization by serum. A measured sample of blood serum to be tested was mixed with a measured excess amount of powdered cholesterol by gentle shaking, or by rotation. The time course of uptake by the serum was determined by measuring cholesterol in the serum after various time intervals of mixing with sonicated cholesterol by rotation at 40 rpm. The results are shown in FIG. 1. At 37°C, the uptake was linear for about 8 hours, and a plateau was reached after 10 to 12 hours and maintained beyond 18 hours. The uptake was considerably slower at room temperature (22°C) and was not appreciable at 6°C. This experiment was repeated with several sera. The cholesterol content at the start of the experiment and values at the plateau varied, but the general characteristic of the time course of uptake and the time required to reach the plateau were similar. The rate of uptake was affected by the dimensions of the vessel, the volume of serum incubated and the rate of rotation. Using the 3 ml Vacutainer tube, 0.5 ml serum and 7 mg of sonicated cholesterol, maximum rate of uptake was achieved when the mixture was incubated and rotated at 30 to 60 rpm at 37°C. When the mixture was incubated and rotated longer than 20 hours, the viscosity of the serum increased and rendered the serum difficult to filter.

For effective mixing of serum with the cholesterol, the optimum rate of rotation of the mixture was found to be between 30 to about 60 rpm. Under the described conditions, the time required to reach quilibrium between unsolubilized and solubilized cholesterol is about 10 to 12 hours, which can be achieved by incubation at 37°C overnight.

As the value for SCBR appeared to increase at elevated temperatures, it was necessary to know whether or not the value changed during the incubation of the serum at 37°C during determination of SCBR. Eight serum samples were preincubated at 37°C for 16 hours and then subjected to the routine procedure for SCBR determination. The values of SCBR with and without the preincubation are listed in TABLE 2. The results indicate that incubation at 37°C for 16 hours did not cause appreciable change in SCBR.

TABLE 2

Effect of Preincubation at 37°C for 16 hours on SCBR

| Serum no. | SCBR | |
|---|---|---|
| | without pre-incubation | preincubated at 37°C for 16 hours |
| | mg/100 ml | mg/100 ml |
| 23 | 83 | 83 |
| 25 | 43 | 64 |
| 27 | 90 | 90 |
| 30 | 53 | 53 |
| 50 | 72 | 79 |
| 77 | 57 | 64 |
| 80 | 52 | 42 |
| 89 | 46 | 50 |

In step (c) the excess cholesterol is removed from the serum after incubation by suitable means, such as filtration. In a preferred embodiment of this invention a tube about 5 mm inside diameter and about 10 cm in length, is fitted at one end with a suitable filter disc. For example, a disc of Whatman No. 30 low ash filter paper is fixed to the tube by adhesive tape. This device allows the incubated serum to filter through, but retains the excess cholesterol.

Steps (b) and (c) can be simplified for routine determinations by use of a tube of suitable dimensions, prefilled with a measured amount of the finely divided cholesterol of step (a) and closed or stoppered. The prefilled tubes, conveniently made of a disposable material such as glass or plastic, can be fitted into a kit sized to hold the prefilled tubes, with suitable filters described in step (c) and such supplies of chemical reagents as are needed for the cholesterol determination in step (d). Instructions for use may also be enclosed in the kit. Preferably the tubes and filters are secured in place by suitable means so as to avoid damage.

In step (d), cholesterol determinations were performed manually, using the Hycell Cholesterol Reagent, to obtain the test results disclosed herein. For studies of SCBR involving larger numbers of serum specimens, known automated procedures such as those used in the determination of serum cholesterol in clinical laboratories can be used.

Figure 1:
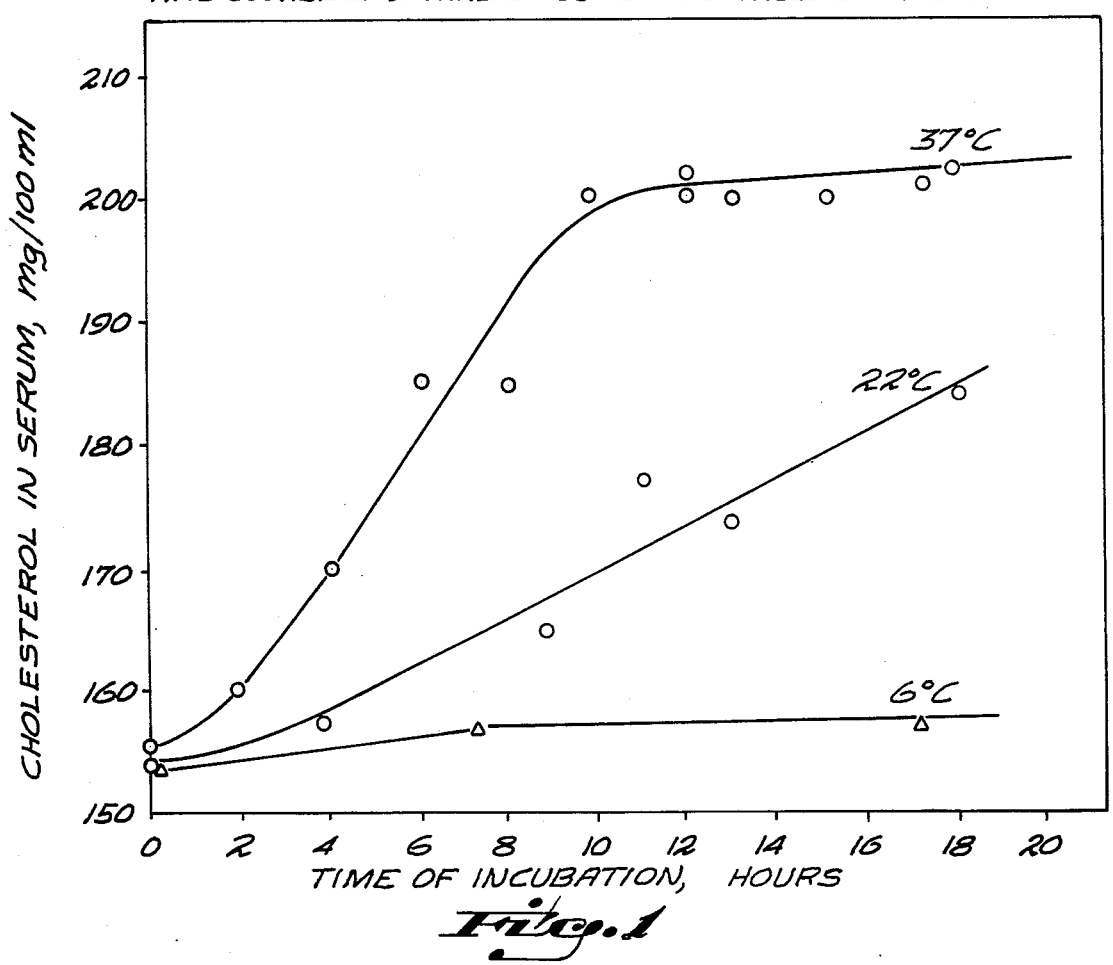
FIG. 1 shows the time course uptake of sonicated cholesterol by serum.

The following preferred method was used for evaluation of large numbers of sera samples:

EXAMPLE 1

Solubilization of cholesterol by serum

Crystalline cholesterol, when incubated and mixed with human serum, dissolves only slowly, and several days are required to reach equilibrium. Prolonged incubation is not only time-consuming, but also causes deterioration of the serum. To facilitate solubilization, it was necessary to reduce the size of cholesterol crystals. Crystalline cholesterol (Eastman Kodak Co., Rochester, N.Y.) was suspended in water (5 ml per gram of cholesterol), and the suspension was subjected to sonication while chilled in an icebath. A Sonifier Cell Disruptor (Model 1850, Heat Systems Ultrasonics, Inc.) was used for seven 2 minute intervals, with 2 minute interruptions to allow cooling of the mixture. The water was removed by filtration and the finely pulverized cholesterol was air-dried at room temperature. Microscopic examination of the cholesterol before and after sonication revealed greatly reduced size of the crystals by sonication.

Incubation

To prepare for the determination of SCBR, 7 mg of the sonicated cholesterol was mixed with 0.5 ml of serum in a 3 ml red top Vacutainer (Becton Dickinson and Co.). The tube was tightly stoppered and placed on a Multipurpose Rotator (Scientific Industries) operating at 40 rpm at 37°C for 15 hours.

Filtering

The serum was then filtered at room temperature through a specially made filter to remove the undissolved cholesterol. The filter was fashioned by fixing a disk of Whatman filter paper No. 30 across one open end of a glass tube (ID 5 mm. approximately 10 cm in length). The edge of the filter paper was sealed tightly around the tube with an adhesive tape. The filtration usually took about 2 hours to complete.

Determination of SCBR

The Liebermann-Burchard reaction, B. Zak et al, Anal. Chem. 33 p. 1405–1407 (1961), was used to determine cholesterol in 0.10 ml of the serum, before and after incubation with the sonicated cholesterol, using the Hycell Cholesterol Reagent (Hycell, Inc.), according to the procedure given by the manufacturer. A Turner Model 350 Spectrophotometer (Turner Associates) was used to measure absorbance at 625 mm. Monitrol (Dade Reagents) and recrystalized cholesterol were used as standards. The reproducibility of results was within ± 5 percent. SCBR was calculated by subtracting the value of cholesterol content in the serum before incubation with the sonicated cholesterol from the value obtained after the incubation and filtration.

Reproducibility of results

In multiple determinations of SCBR of two sera, the results were 67,68,57,57,51 mg/100 ml for one (mean = 60 ± 7 mg/100 ml), and 79,89,67 and 86 mg/100 ml for the other (mean = 80 ± 10 mg/100 m.). The errors of these determinations were ± 11 percent.

Individual variations in SCBR

Using the above described method, serum specimens were examined from more than 200 men and women, between the age of 30–60 years. The values of SCBR varied from individual to individual and ranged from 0 to 226 mg/100 ml. Repeated serum samples were obtained from some individuals, and SCBR remained unchanged for several weeks. For example, the values for SCBR of one indivual over 4 weeks were 78,86,71 and 80 mg/100 ml, and values of another individual over 5 weeks were 70,63,59 and 75 mg/100 ml. The variations were within the error of method of determination.

SCBR in premature myocardial infarction

Subjects were chosen from the case-control study of myocardial infarction in Specialized Center of Research for Study of Atherosclerosis in Childhood at the University of Miami School of Medicine. Blood specimens were obtained from the antecubital vein and allowed to clot. SCBR determinations were performed by the same technician, without knowledge of the status of the subject, within 24 hours after the blood was drawn. Cases were white males between the age of 30–50 years, who had experienced a myocardial infarction documented by World Health Organization criteria, at least 6 months previously. Controls were matched on race, sex, age and neighborhood of residence. Since the matching factors were not confounding within these data, and hence, did not enhance validity, unmatched analysis were performed for statistical efficiency.

Figure 2:
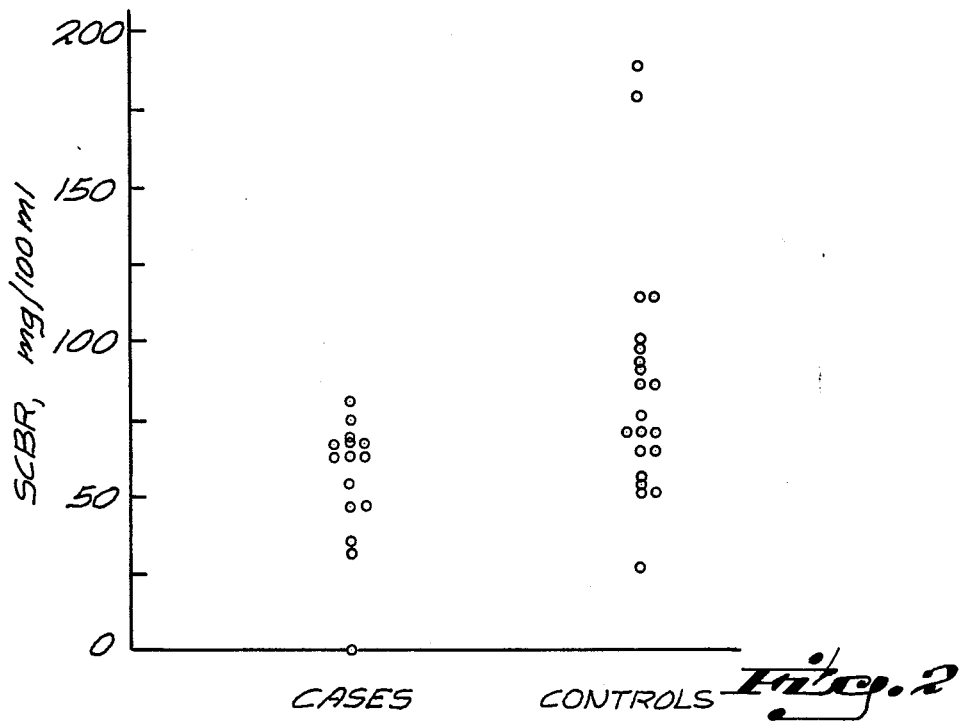
FIG. 2 shows the serum cholesterol binding reserve of cases and controls.

The values of SCBR of 15 cases and 21 controls are shown in FIG. 2. There is a distinct trend of lower values from the cases and there is considerable overlapping of values from cases and controls in the range of 55 to 75 mg/100 ml. A statistical treatment of these data and values of SC is presented in TABLE 3.

TABLE 3

SC and SCBR of cases with myocardial infarction and controls

|  | SC | SCBR | SCBR/SC | SC/(SC + SCBR) |
|---|---|---|---|---|
|  | mean ± SD | mg/100 ml |  | % |
| Cases (N = 15) | 255 ± 79 | 55 ± 21 | 0.24 ± 0.10 | 81.3 ± 7.2 |
| Control (N = 21) | 225 ± 42 | 85 ± 38 | 0.38 ± 0.16 | 73.4 ± 7.6 |
| p* | 0.25+ | 0.01 | 0.005 | <0.004 |

*Obtained by t-test for independent samples.
+Logarithmic transformation was performed to achieve homogeneity of variances.

The mean ± SD of SC of cases (255 ± 79 mg/100 ml) was higher than that of controls (225 ± 42 mg/100 ml), but the difference was not significant, (p = 0.25). However, the difference of SCBR between cases and controls (55 ± 21 and 85 ± 38 mg/100 ml, respectively) was significant (p <0.01).

SCBR/SC and SC/(SC + SCBR) are indices of atherogenic activity.

The same parameters among wives of cases and controls are compared in TABLE 4. No difference between the two groups would be expected and none was found.

TABLE 4

SC and SCBR of wives of cases of premature myocardial and wives of controls

|  | SC | SCBR | SCBR/SC | SC/(SC + SCBR) |
|---|---|---|---|---|
|  | mean ± SD | mg/100 ml |  | % |
| Wives of Cases (N = 11) | 215 ± 29 | 85 ± 20 | 0.402 ± 0.106 | 71.7 ± 5.4 |
| Wives of Controls (N = 21) | 224 ± 56 | 86 ± 26 | 0.401 ± 0.144 | 72.1 ± 7.5 |
| p* | 0.42 | 0.94 | 0.55 | 0.88 |

*Two sided p values were obtained by t-test for independent samples.

Of the 15 cases, 10 (66.7 percent) had SC greater than 225 mg/100 ml, the mean SC of controls; while SC of 10 of the 21 controls (47.6 percent) was above this value. The difference between these proportions was not significant ($p = 0.26$). On the other hand, all of the 15 cases (100 percent) and 11 of the 21 (52.4 percent) controls had SCBR less than 85 mg/100 ml, the mean SCBR of controls. The difference between these proportions was significant ($p = 0.005$).

In order to compare the ability of SCBR with that of SC to discriminate between cases and controls, a discriminant function analysis was performed, and the result indicated that SCBR was a better discriminant than SC ($p = 0.023$).

The degree of saturation of the serum with cholesterol SC/(SC + SCBR) was 81.3 ± 7.2 percent among cases and 73.4 ± 7.6 percent among controls. The difference between these means was highly significant ($p < .004$). The ratio SCBR/SC was 0.24 ± 0.10 among cases and 0.38 ± 0.16 among controls. The difference between these means was also highly significant ($p = .005$).

To summarize, the data in TABLE 3 revealed that the values of SCBR of cases of premature myocardial infarction were statistically lower than that of the controls ($p = 0.01$), although within the small sample of this study the difference in SC did not achieve statistical significance. As the mean of SC of cases was higher than that of controls, the ratio SCBR/SC and the degree of saturation of the serum with cholesterol, SC/(SC + SCBR), were consequently more significantly different between the two groups than either SC or SCBR was. It appears that a balance of forces between SC and SCBR may exist in atherogenesis, so that In contrast to findings presented in TABLE 3, the data in TABLE 4, as expected, indicated no statistical differences in SC, SCBR or their combinations, between the wives of cases and controls. It is interesting that the mean of SCBR of these women (85 ± 20 and 86 ± 26 mg/100 ml), who had no clinical manifestation of coronary abnormality, was in the same range as that of the male controls (85 ± 38 mg/100 ml).

Discriminant function analysis using the data in TABLE 3 further indicated that SCBR is a stronger discriminant between cases and controls than SC. The findings indicate that SCBR is a risk factor of coronary heart disease, such that lower the SCBR, the higher the risk of coronary heart disease.

The values of SCBR, SCBR/SC ratio and SC/(SC + SCBR) are likewise useful for correlation with other clinical test data for a particular individual relating to the known incidence of other factors predisposing that individual toward atherosclerosis or heart disease, such as diabetes, hypertension, overweight, certain diseases of the liver, familial hypercholesterolemia, and other maladies.

What is claimed is:

1. A method for determining serum cholesterol binding reserve of human blood serum which comprises the steps of:
   a. admixing in predetermined amounts an excess amount of finely divided cholesterol with a specimen of blood serum;
   b. incubating the mixture for a period of time and at temperatures sufficient to maximize the solubilization of cholesterol in the serum while obtaining continuous contact of said serum with said cholesterol by suitable means;

c. separating the incubated serum of step (b) from the excess of cholesterol; and thereafter d. measuring the amount of cholesterol in said incubated serum, and subtracting from this amount the measured cholesterol content of a reference specimen of the same serum prior to incubation with cholesterol.

2. The method of claim 1 wherein said finely divided cholesterol of step (a) is prepared by sonication of a suspension of the cholesterol in water while maintaining the temperature within the range of about 0°C to 10°C during sonication, filtering, and then air-drying at room temperature.

3. The method of claim 1 wherein said finely divided cholesterol in step (a) is prepared by dispersing on an inert solid media in powderous form.

4. The method of claim 1 wherein said incubation in step (b) takes place in a tightly stoppered tube which is placed in a rotating mixer operating at about 30 to 60 RPM during incubation.

5. The method of claim 1 wherein step (a) is simplified by use of a disposable tube of suitable dimensions prefilled with a measured amount of said finely divided cholesterol.

6. The method of claim 1 wherein said serum is filtered in step (c) using a filter tube of suitable dimensions which is fitted at one open end with a filter disc.

7. A method of obtaining reproducible results ± 11% for the serum cholesterol binding reserve of blood serum in mg of cholesterol solubilized per 100 ml of serum, which comprises the steps of:

a. pulverizing crystalline cholesterol into very small particles by sonicating a suspension of about 1 gram of crystalline cholesterol in about 5 ml of water maintained at a temperature within the range of about 0°C to 10°C for about seven 2 minute intervals, with about 2 minute interruptions for cooling between sonications; filtering off the water; and air-drying at room temperature;

b. incubating at about 37°C for about 15 hours 0.5 ml of blood serum which has been kept at room temperature for not more than 2 to 3 days, or kept frozen at about −20°C for not more than several months, with about 7 mg of said sonicated cholesterol of step (a) in a tightly stoppered tube which is placed on a rotator operating at about 40 RPM;

c. separating the serum from the undissolved cholesterol by filtering at room temperature through a filter tube fashioned by fixing a disk of filter paper of the proper size across one open end of a tube having an ID of about 5 mm, and an approximate length of 10 cm, the edge of the filter paper being sealed tightly around the tube; and thereafter d. determining the amount of cholesterol in about a ml sample of serum after incubation; and e. subtracting the value for cholesterol content in a reference specimen of the same serum before incubation with said sonicated cholesterol from the value obtained after the incubation and filtration to obtain the value for serum cholesterol binding reserve.

8. A method for early warning of risk of atherosclerosis, so as to assess the risk of coronary heart disease in humans, employing values for the serum cholesterol binding reserve of human blood serum obtained by the steps of:

a. admixing in predetermined amounts an excess amount of finely divided cholesterol with a specimen of blood serum;

b. incubating the mixture for a period of time and at temperatures sufficient to maximize the solubilization of cholesterol in the serum while obtaining continuous contact of said serum with said cholesterol by suitable means;

c. separating the incubated serum of step (b) from the excess of cholesterol; and thereafter d. measuring the amount of cholesterol in said incubated serum, and subtracting from this amount the measured cholesterol content of a reference specimen of the same serum prior to incubation with cholesterol.

* * * * *